United States Patent [19]
Sakai

[11] Patent Number: 4,794,949
[45] Date of Patent: Jan. 3, 1989

[54] VALVE WITH RESIDUAL PRESSURE INDICATOR FOR PORTABLE OXYGEN INHALANT CYLINDER

[75] Inventor: Mitsunori Sakai, Amagasakishi, Japan

[73] Assignee: Kabushiki Kaisha Neriki, Hyogoken, Japan

[21] Appl. No.: 102,488

[22] Filed: Sep. 29, 1987

[30] Foreign Application Priority Data

Oct. 14, 1986 [JP] Japan ................. 61-243497

[51] Int. Cl.⁴ .................................. F16K 37/00
[52] U.S. Cl. ........................... 137/557; 73/744
[58] Field of Search ........... 137/557; 73/146.3, 146.8, 73/714, 744

[56] References Cited

U.S. PATENT DOCUMENTS

| | | | |
|---|---|---|---|
| 2,518,540 | 8/1950 | Green | 73/744 |
| 3,203,246 | 8/1965 | Horwitt et al. | 73/744 |
| 3,365,950 | 1/1968 | Park | 73/744 |
| 3,455,167 | 7/1969 | Bateson | 73/744 |
| 3,554,225 | 1/1971 | Debenedetto | 137/557 |
| 3,910,120 | 10/1975 | Martin | 73/744 |
| 4,580,450 | 4/1986 | Ota et al. | 73/313 |
| 4,622,857 | 11/1986 | Nelson | 137/557 X |

FOREIGN PATENT DOCUMENTS

| | | | |
|---|---|---|---|
| 1299533 | 7/1969 | Fed. Rep. of Germany | 73/744 |
| 921990 | 5/1947 | France | 73/744 |
| 2108670 | 5/1983 | United Kingdom | 73/744 |

Primary Examiner—John Rivell
Attorney, Agent, or Firm—Foley & Lardner, Schwartz, Jeffery, Schwaab, Mack, Blumenthal & Evans

[57] ABSTRACT

The present invention relates to a valve with a residual pressure indicator for a portable oxygen inhalant cylinder, which is a small-sized valve secured to a mouth portion of such portable small cylinder in which the inhalant oxygen is charged in a pressurized state. A residual pressure indicator is assembled in the valve casing of the valve so that a residual amount of compressed oxygen within the cylinder is observed accurately from an outside of the valve casing. Accordingly, the oxygen inhalation device provided with the valve can be safely carried by a patient who has pulmonary disease or respiratory disease or rescuers.

12 Claims, 7 Drawing Sheets

VALVE WITH RESIDUAL PRESSURE INDICATOR FOR PORTABLE OXYGEN INHALANT CYLINDER

BACKGROUND OF THE INVENTION

1. Field of the Invention

The present invention relates to a valve with a residual pressure indicator for a portable oxygen inhalant cylinder, which is provided for an oxygen inhalant cylinder used by a patient who has pulmonary disease or respiratory disease or carried by a doctor or rescuers at a rescue operation, and of which valve casing is provided with a residual pressure indicator at the lower half thereof which indicates a residual oxygen pressure in the cylinder (inner volume: ab. 3 l).

2. Prior Art

Recently, thanks to a medical progress there is an increasing number of patients who go out with the aid of an oxygen walker even though such patients always need the oxygen inhalants due to their pulmonary disease or respiratory disease.

In case the oxygen in the cylinder is emptied during their outing or during rescue dispatching, such patients get into difficulty in breathing and encounter a fatal danger. Therefore, in order to prevent such dangerous situations, it is necessary that the sufficient amount of residual oxygen in the cylinder is confirmed prior to leaving by means of the residual pressure indicator.

A valve with a residual pressure indicator for a portable oxygen inhalant cylinder according to the present invention has a basic construction, for example as shown in FIG. 1 or in FIG. 7.

That is, in an upper half of a valve casing 6, there is provided a valve chamber 8 which has an inlet port 9 opened at the bottom surface of the casing 6 as well as an outlet port 10 opened at the side surface thereof and also has a valve body 11 located therein. At the upper side of the valve casing 6, there is provided a handle 12 which is used for opening and closing the valve body 11, and at the lower half of the valve casing 6, there is provided a residual pressure indicator 13 for an oxygen cylinder.

As for a construction for setting the residual pressure indicator on the valve such is known in the conventional first embodiment as shown in FIG. 7.

In this embodiment, a residual pressure conduction port 50 is transversely branched off from the intermediate portion of the inlet port 9 and opened at the lower half side surface of the valve casing 6. And to the outer end portion of the residual pressure conduction port 50, a Bourdon tube pressure gauge 51 is fixedly connected in communication by means of its foot screw 51a.

Besides the oxygen inhalant application and the premised construction as described above, the conventional second embodiment as shown in FIGS. 8 and 9 has so far been placed on the market as a valve provided with a primary pressure indicator in a pressure reduction valve which is detachably connected to a liquefied carbon dioxide container for a draught beer feeder.

FIG. 8 is a plan view of the pressure reduction valve 53, in which carbon dioxide gas in the container 54 is induced to a primary pressure inlet 53a from the container valve 55 while the primary pressure is indicated by the primary pressure indicator 56, then reduced in pressure within a pressure reduction valve body 57 and discharged from a secondary pressure outlet 53b while the secondary pressure is indicated by a secondary pressure indicator 58.

FIG. 9 is a vertical sectional view of the primary pressure indicator 56 of an air pressure operational cylinder type which has a pressure receiving piston counterbalanced by a balance spring. It is fixedly secured to the side surface of the pressure reduction valve body 57 so as to project laterally by means of screws. When the primary pressure is transmitted to a cylinder chamber 59 through a primary pressure discharge pot 57a and the pressure in a container 54 gets a fully charged pressure, the piston actuates a residual pressure indicating rod 61 so as to project a residual pressure indicating ring 62 thereof a large distance outside a cover 63. As the residual pressure is decreased, the indicating ring 62 is shifted toward the cover 63 by the balance spring 64. When the residual pressure in the container has decreased to ab. 20 $Kg/cm^2$, the indicating ring 62 enters the cover and is concealed therein.

Further, in spite of being from a different field than the third embodiment another valve is disclosed in U.S. Pat. No. 4,580,450 by the assignee of the present invention.

As shown in FIG. 10, in the side wall of a valve casing 71 of a high pressure valve 70 for a vertical elongated cylindrical container C for liquefied carbon dioxide, there is provided a vertical guide hole 72 formed as a blind hole upwardly from the lower surface 73 of the valve casing 71 over the whole of its height. In this guide hole 72, there is provided a residual quantity detecting means 74 movable in the vertical direction. The detecting means is connected to an elongated cylindrical float 76 through a rod 75. The float 76 is received in the container C movably in the vertical direction. The rod 75 is biassed downwardly by an extension spring 77 held by the valve casing 71. At the level corresponding to the residual quantity detecting means 74 outside the peripheral wall of the guide hole 72, there is provided a residual quantity indicating means 78 so as to indicate a residual quantity of liquefied carbon dioxide in the container C. The indicating means 78 is adapted to be moved vertically by the detecting means 78 through magnetic force so that the liquid level in the liquefied carbon dioxide container C can be confirmed visually with the residual quantity indicating means 78.

The conventional first embodiment shown in FIG. 7 has for its advantages large pressure-resistance as well as high accuracy for indicating a residual pressure because the residual pressure in the container is detected by a deformation of a Bourdon tube under pressure, but has for its disadvantages following problems:

(a) The Bourdon tube pressure gauge 51 has a magnifying mechanism of a gear type for magnifying a very small displacement caused by a deformation of a Bourdon tube under pressure, which serves to drive a pointer on a graduated plate in a magnified manner by making use of a pinion having fine teeth. Further, since the Bourdon tube pressure gauge 51 is small enough to be used for the small portable oxygen inhalant container 1 correspondingly, the teeth of the pinion becomes finer and weaker against a shock as the result.

In case that the teeth of the pinion become damaged when the pressure gauge 51 is shocked by its falling or its collision with other objects, the pointer is apt to be locked. Thus, in the case of using it without noticing such trouble, the pointer is kept indicating a high pressure even though a residual pressure in the container has decreased to a large extent. As a result, in spite of the confirmation of enough residual pressure of oxygen by the patient before outing, it is possible that the patient gets into a fatal danger because the oxygen is almost exhausted during an outing.

(b) Since the Bourdon tube pressure gauge 51 is secured to the valve casing 6 in an outward projecting manner, it is apt to be broken by a shock caused by its falling or its collision with other objects. In such a case, it is also possible that the patient gets into a fatal danger because the oxygen escapes completely from the container through the breakage portion.

Even though the patient gets out of such danger, the Bourdon tube pressure gauge 51 is always in danger of breakage by collision with other objects because it projects outside the valve casing 6.

The Bourdon tube pressure gauge 51 of the conventional first embodiment as shown in FIG. 7 can be replaced with the primary pressure indicating means 56 of the conventional second embodiment 2 as shown in FIGS. 8 and 9. In the combined construction of these first and second conventional embodiments, since it is adapted to transmit the movement of the piston 60 directly to the residual pressure indicating rod 61, it has such advantage as the above-mentioned problem (a) can be solved. However, it still has the problem (b) as well as the following problems. Even though the residual pressure indicating ring 62 indicates ab. 20 Kg/cm$^2$ at the position near the entrance of the cover 63, it is still difficult to know a residual pressure in the container when the ring 62 is outside the cover or within the cover 63.

On the other hand, the third conventional embodiment is applied to a relatively large container C for liquefied carbon dioxide in an entirely different field from the present invention. And since the residual quantity indicating means is adapted to be moved correspondingly by the vertical movement of the float 76, it can't be applied to the small-sized light gas cylinder which is charged with compressed oxygen for an oxygen inhalation. Further, also in this third conventional embodiment, since the residual quantity indicating means 78 is attached to the valve casing 71 in an outwardly projecting manner, it is impossible to avoid the risk of the breakages of the indicating means 78 by its falling or by its collision with other objects.

SUMMARY OF THE INVENTION

The present invention is directed to solving the problems noted above. Therefore, it is an object of the present invention to provide a valve with a residual pressure indicator for a portable oxygen inhalant cylinder which enables one to accurately indicate a residual pressure within a gas cylinder by improving the vibration-proof as well as the shock-proof of the residual pressure indicator. It is another object of the present invention to provide a valve with a residual pressure indicator for such a cylinder which enables one to prevent breakage or damage of the residual pressure indicator which might be caused by a collision with other objects. It is a further object to provide such a valve which enables one to know the accurate residual pressure within a gas cylinder over a wide range from a high pressure to a low pressure.

The means for accomplishing the above purpose is characterized in that in the above-mentioned construction, a residual pressure measuring chamber is provided vertically at the portion beside the inlet port in the lower half of the valve casing, a through hole for a pressure actuator bar is opened downwardly from the lower end portion of the residual pressure measuring chamber, a sealing means is provided at the through hole so as to make contact with the intermediate portion of the pressure actuator bar and permit the vertical sliding movement thereof, a balancing spring is connected to the lower portion of the pressure actuator bar so as to elastically force the bar downwardly, and a residual pressure indicating means is provided onto the pressure actuator bar so as to move vertically within the residual pressure measuring chamber.

According to the present invention, as shown in FIG. 1, the pressure actuator bar is moved upwardly within the through hole against the elastic force of the balancing spring under a high residual pressure condition within the oxygen inhalant cylinder, and the residual pressure indicating means is shifted to an upper position within the residual pressure measuring chamber. Accordingly, the amount of residual oxygen within the cylinder can be confirmed by observing the level of the indicating means through a peep window.

On the other hand, as the residual pressure is decreasing due to a consumption of oxygen within the cylinder, the elastic force of the balancing spring exceeds the pressure force acting on the pressure actuator bar and moves the bar downwardly so as to shift the residual pressure indicating means to a lower position in the residual pressure measuring chamber. A less amount of residual oxygen within the cylinder is confirmed by observing the indicating means shifted lower than a predetermined level through the peep window.

The foregoing and other objects and attendant advantages of the present invention will be readily appreciated as the same becomes better understood by reference to the following detailed description when considered by the accompanying drawings, wherein:

BRIEF DESCRIPTION OF THE DRAWINGS

FIGS. 1 through 4 show the first embodiment thereof;

FIG. 1 is a vertical sectional view showing a valve with a residual pressure indicator for a portable oxygen inhalant cylinder;

FIG. 2 is an exploded perspective view of an oxygen inhalant device;

FIG. 3 is an enlarged view of a principal part in FIG. 1;

FIG. 4 is a sectional view on line IV—IV in FIG. 3;

FIGS. 5 and 6 show the second embodiment of the present invention;

FIG. 5 is a view corresponding to FIG. 3;

FIG. 6 is a sectional view on line VI—VI in FIG. 5;

FIG. 7 is a sectional view of the first embodiment thereof;

FIGS. 8 and 9 show the second embodiment thereof;

FIG. 8 is a plan view thereof;

FIG. 9 is a sectional view on line IX—IX in FIG. 8; and

FIG. 10 is a sectional view of a principal part of the third embodiment.

DETAILED DESCRIPTION OF PREFERRED EMBODIMENTS

Now the preferred embodiments of the present invention will be described with reference to the drawings hereinafter.

<FIRST EMBODIMENT>

FIGS. 1 through 4 show the first embodiment.

Figure 2:
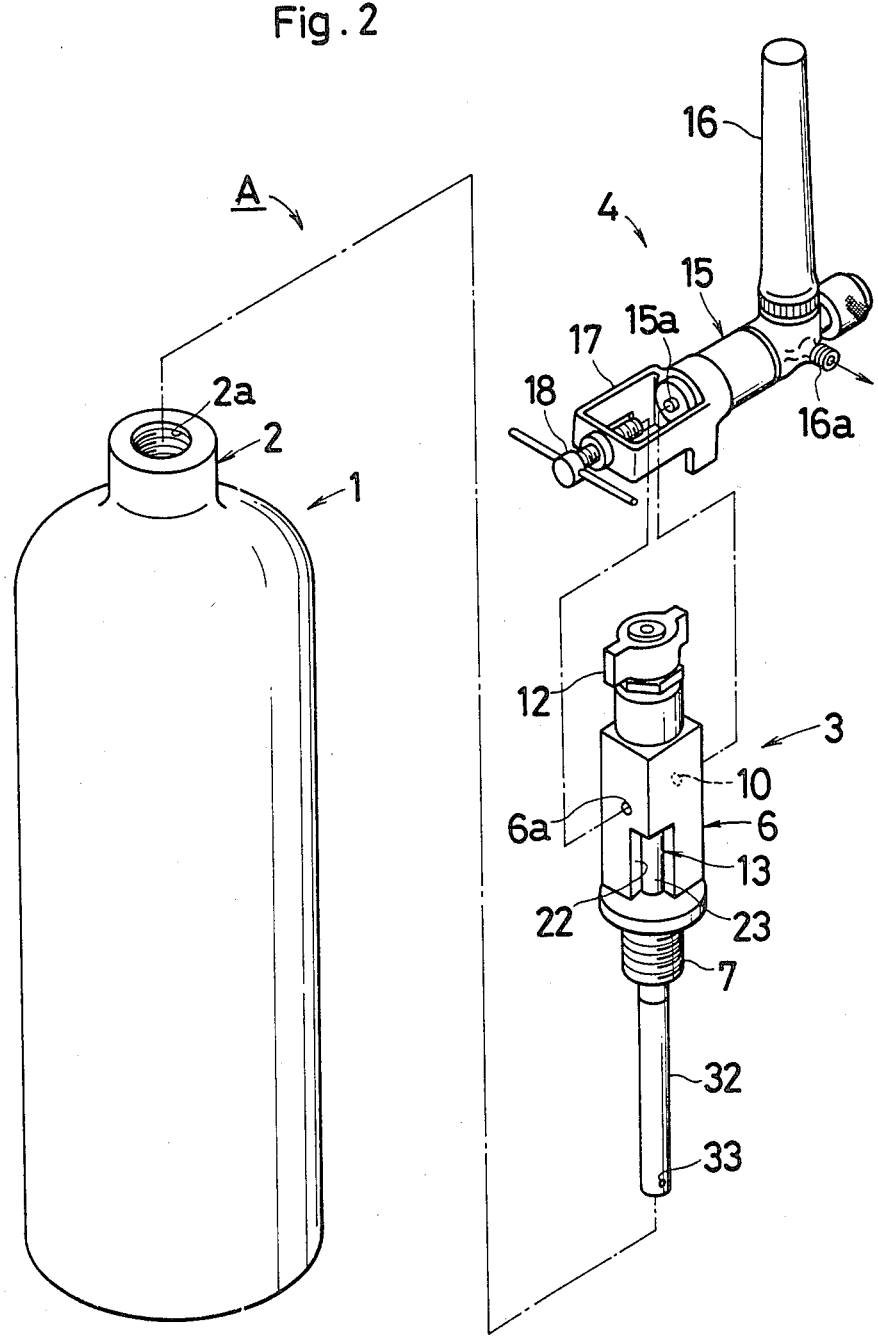

FIG. 2 is an exploded perspective view of a portable oxygen inhalant device A.

Figure 1:
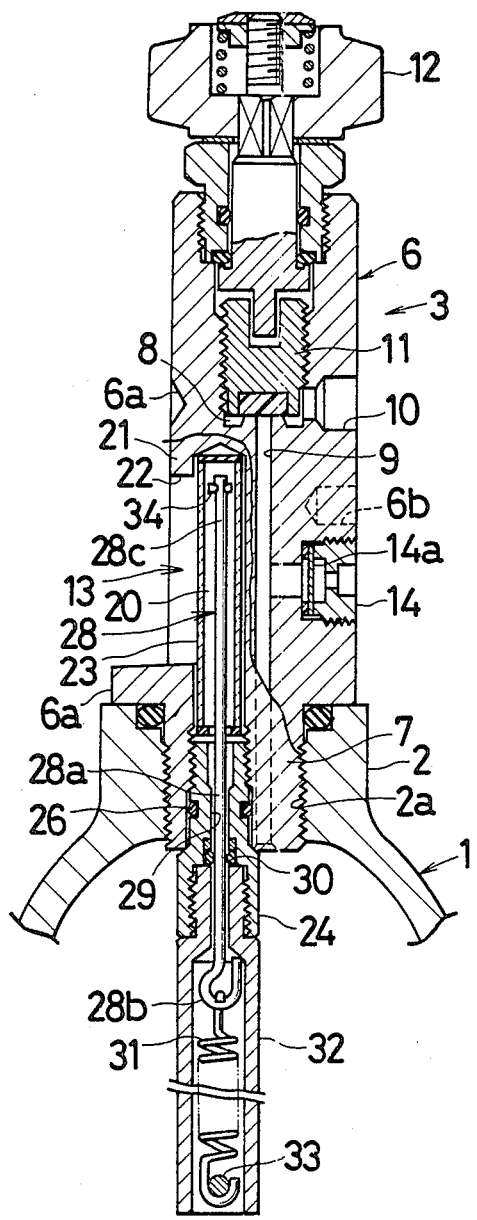
FIGS. 1 through 6 show the embodiment of the present invention.

Referring to FIGS. 1 and 2, a valve 3 is fixedly secured to an inlet 2 of an oxygen inhalant cylinder 1, and an oxygen withdrawing 4 is adapted to be connected to the valve 3. The oxygen inhalant device A is of a size to be carried out with a portable case (not shown in Figs.), and to be utilized for the aid of inhalation by a patient who has pulmonary disease or respiratory disease so that the oxygen charged into the cylinder 1 can be taken out through the valve 3 and the oxygen withdrawing means 4.

First of all, mainly the valve 3 will be explained with reference to FIG. 1.

The valve 3 has a valve casing 6 which is rectangular in a plan view, a foot portion 7 which is fixedly screwed into a threaded hole 2a provided at the inlet 2 of the oxygen inhalant cylinder 1 and a flange 6a which is formed at the lower portion of the valve casing 6 and is abutted onto the upper surface of the inlet 2 gas-tightly. In the upper half of the valve casing 6, there is formed a cylindrical valve chamber 8 of which inlet port 9 is opened at the bottom surface of the foot portion 7 and of which outlet port 10 is at the right side surface of valve casing 6. In the valve chamber 8, there is provided a valve body 11 vertically adjustable which is engaged by a handle 12 provided at the upper portion of the valve casing so as to open or close the valve body 11. At the lower half of the valve casing 6, there is provided a residual pressure indicator 13 which indicates a residual pressure of oxygen within the cylinder 1. And at the right side of the valve casing 6, there is provided a safety valve 14 of a thin plate type which is fixed by a screw plug. 14a is a thin plate for explosion.

Now the oxygen withdrawal means 4 will be explained with reference to FIG. 2 hereinafter.

The oxygen withdrawal means 4 is of a well known type, and is provided with a pressure regulator 15 and a flow meter 16, and is connected to the valve casing 6 of the valve 3 through a box-shaped mount frame 17 which is standardized in dimension.

That is, the mount frame 17 is fitted to the upper half of the valve casing 6 and an inlet nozzle 15a of the pressure regulator 15 is inserted into the outlet port 10 of the valve 3, And then a tightening bolt 18 engaged with the mount frame 17 is inserted into a hole 6a for positioning at the left side of the valve casing 6 and tightened so that the nozzle 15a of the pressure regulator 15 can be fixedly pushed to the outlet port 10 of the valve 3. The oxygen is adapted to be supplied from an outlet nozzle 16a provided at the lower side of the flow meter 16.

By the way, at a position below the inlet nozzle 15a in the mount frame 17, there is provided an engage pin (not shown in Figs.) for positioning which is adapted to be engaged to an engage hole 6b formed at the right side of the valve casing 6 when the mount frame 17 is connected. The dimension and the number of engaging portions between the hole 6b and the pin are determined different according to the kind of gas so that a different kind of gas can't be taken out.

Figure 4:
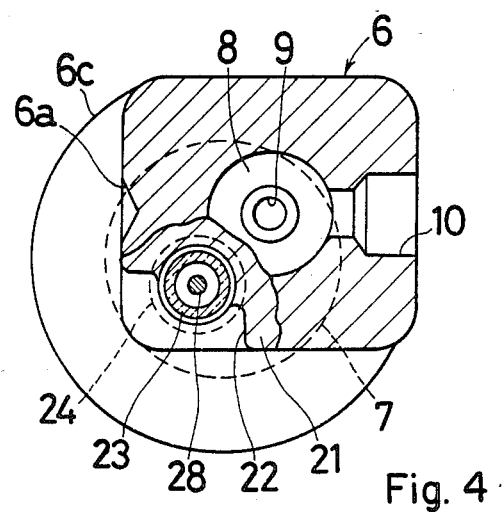
Figure 3:
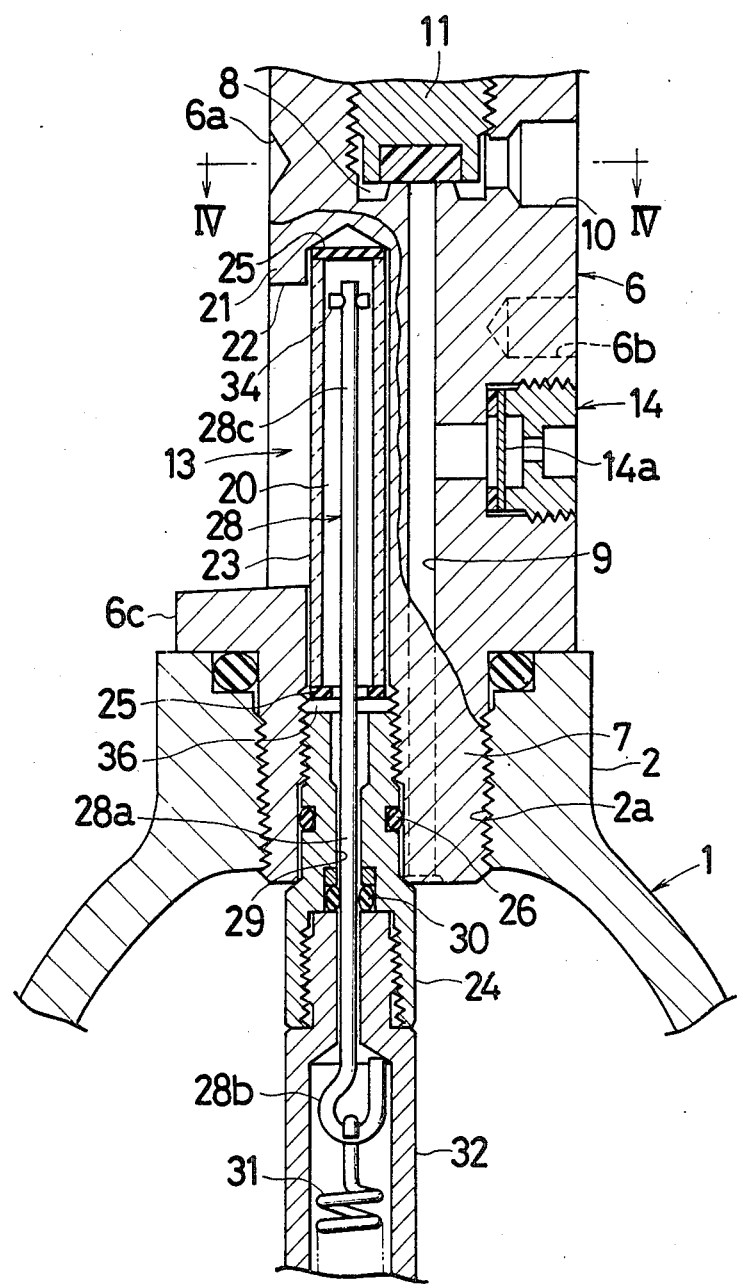

Now the residual pressure indicator 13 provided on the valve 3 as a subject-matter of the invention will be explained mainly with reference to FIGS. 3 and 4 hereinafter.

At a different position within the lower half of the valve casing 6 from the inlet port 9, there is formed a cylindrical residual pressure measuring chamber 20 vertically. In the peripheral wall 21 of the residual pressure measuring chamber 20, there is provided a peep window 22. A transparent resin tube 23 is put in the chamber 20 and provided with a cushion member 25 at the upper and the lower ends thereof respectively. The transparent tube 23 is fixedly pushed to the valve casing 6 by a holder 24 which forms the bottom wall of the chamber 20. The holder 24 is mounted to the foot portion 7 by threaded portions gas-tightly through an O-ring 26.

In the holder 24, there is provided a through hole 29 which is provided with a sealing means 30 in the form of an O-ring through which the pressure actuator bar 28 is passed vertically slidably and gas-tightly at the intermediate portion 28a thereof. A balancing spring 31 for a residual pressure measurement is connected to the lower portion of the pressure actuator bar 28 so as to elastically force the bar 28 downwardly and accommodated within a spring support sleeve 32 which is fixedly screwed in the lower portion of the holder 24. The balancing spring 31 is composed of an extension coil spring, supported at its lower end by a pin 33 provided at the lower end of the sleeve 32 as well as connected at its upper end to the lower portion 28b of the spring actuator bar 28. And at the upper portion 28c of the pressure actuator bar 28, there is provided a residual pressure indicating means 34, which is vertically movable within the transparent tube 23 with the pressure actuator bar 28 and the level of which is capable of being observed through the peep window 22.

At the upper end surface of the holder 24, there is provided a notch 36, through which the interior of the transparent tube 23 is communicated to the open air. Besides, in order to obtain the communicating means for communicating the interior of the transparent tube 23 to the open air, at least one of the upper and the lower cushion members 25, 25 may be made porous ventilatively. Accordingly, even though the oxygen within the cylinder 1 enters into the tube 23 by permeating through the O-ring 26 fitted around the periphery of the holder 24 and/or the O-ring 30 fitted around the inner periphery thereof, the pressure increase within the tube 23 can be avoided. And the transparent tube 23 has graduations (not shown in Figs.) for indicating a residual pressure in the vertical direction.

By the way, in the above-mentioned first embodiment, instead of the transparent tube 23 and the cushion member 25, 25 in the residual pressure measuring chamber 20, the residual pressure indicating means 34 within the chamber 20 may be adapted to be observed directly through the peep window 22. In this case, the graduations can be provided at the inner periphery 21 of the chamber 20 in the vertical direction thereof. Further, instead of the extension spring, a compression spring can be used for the balancing spring 31 because it is enough for the balancing spring 31 only to elastically force the pressure actuator bar 28 downwardly.

According to the present first embodiment, since the balancing spring 31 is provided in the space below the valve casing 6, it is accommodated within the cylinder in the case that the valve 3 is fixedly secured to the cylinder 1. Therefore, the inner space within the cylinder 1 can be utilized so effectively that the height of the valve casing 6 is prevented from being increased even in the case of the provision of the balancing spring 31.

Further, in the first embodiment, the box-shaped mount frame 17 is used for the connecting mans to connect the pressure regulator 15 to the valve 3. But, instead of that, a direct connection by means of thread can be adopted as for the connecting means.

<Second Embodiment>

Figure 6:
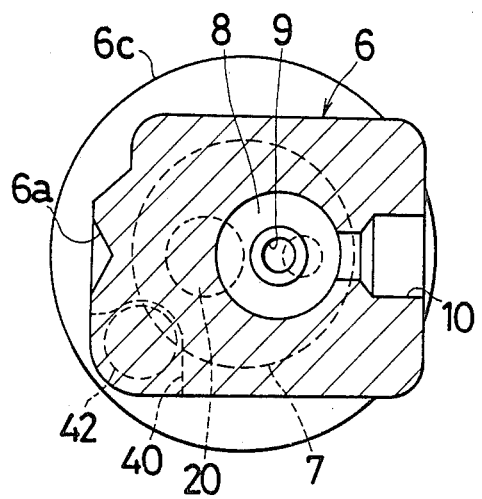
Figure 5:
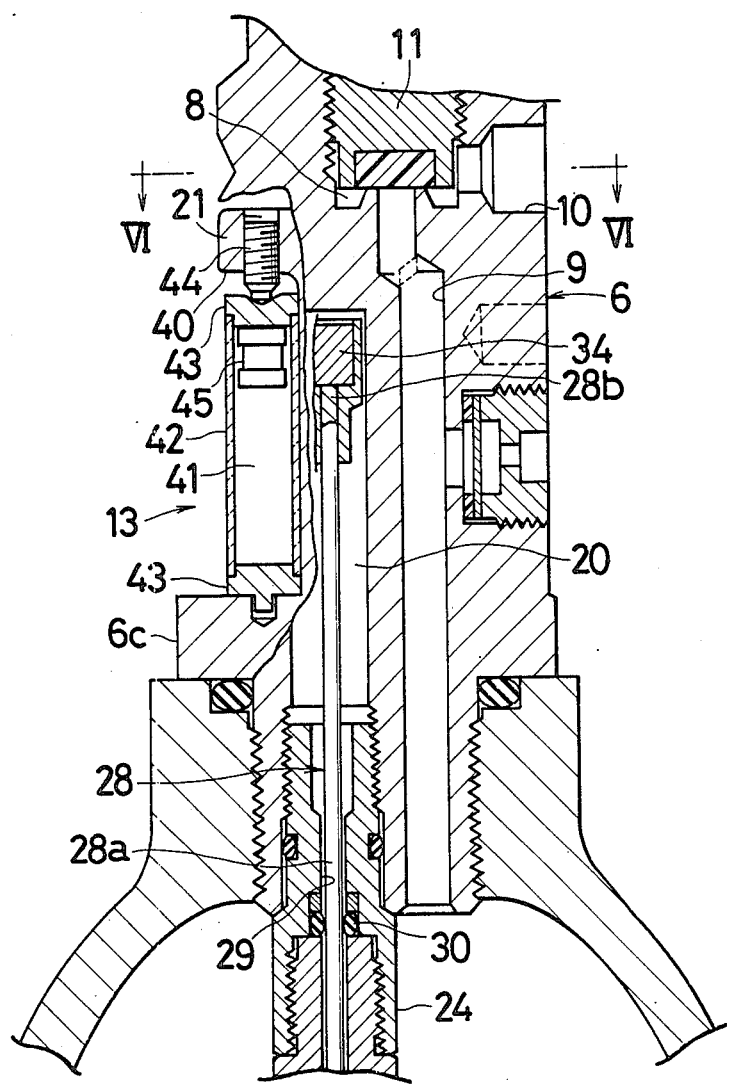
Figure 7:
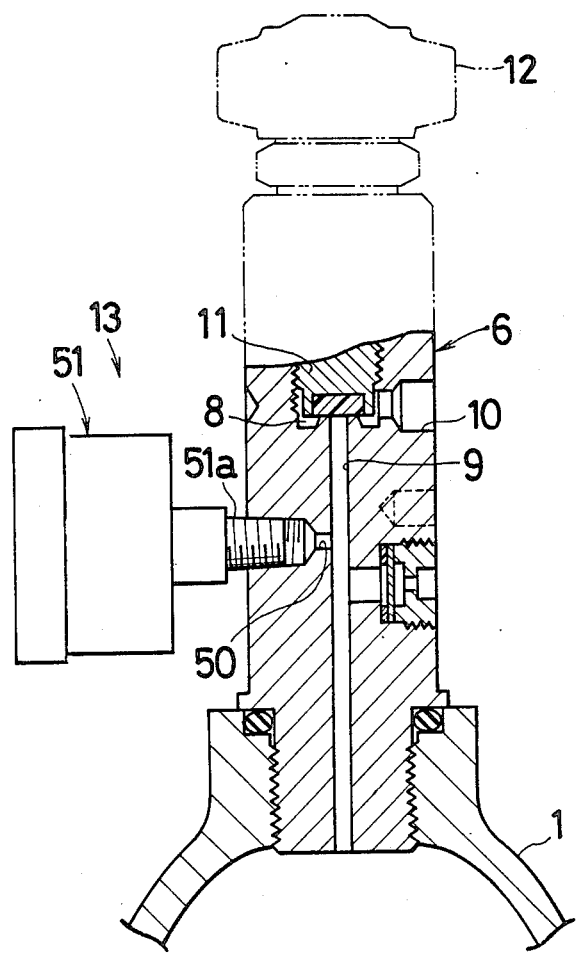
FIGS. 7 through 10 show conventional embodiments.
Figure 8:
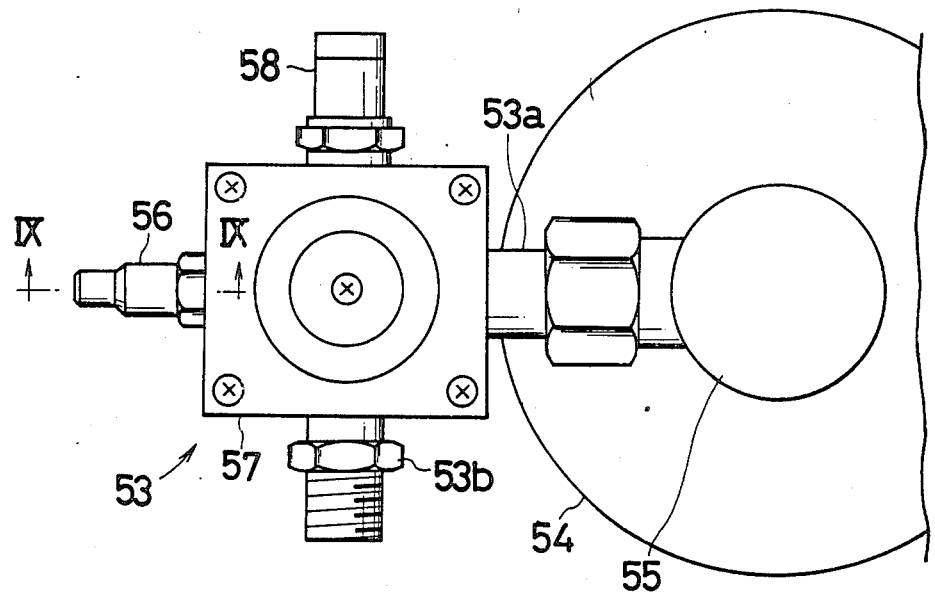
Figure 9:
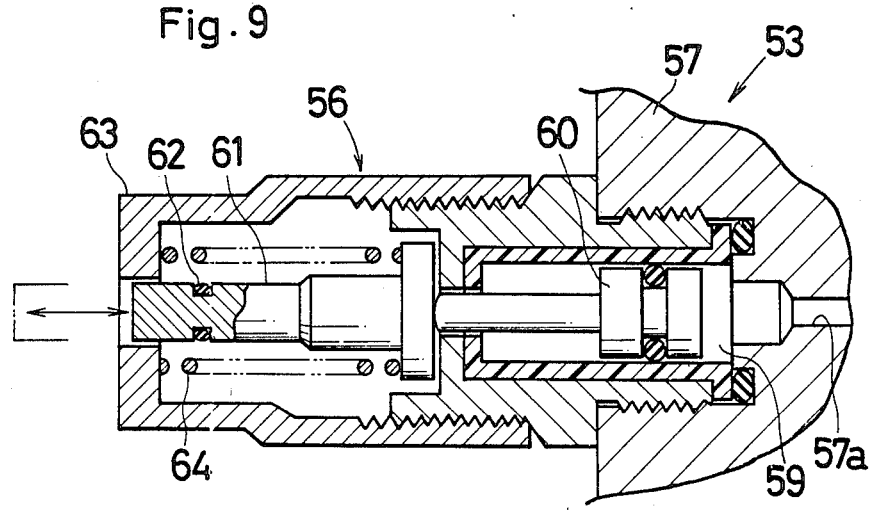
Figure 10:
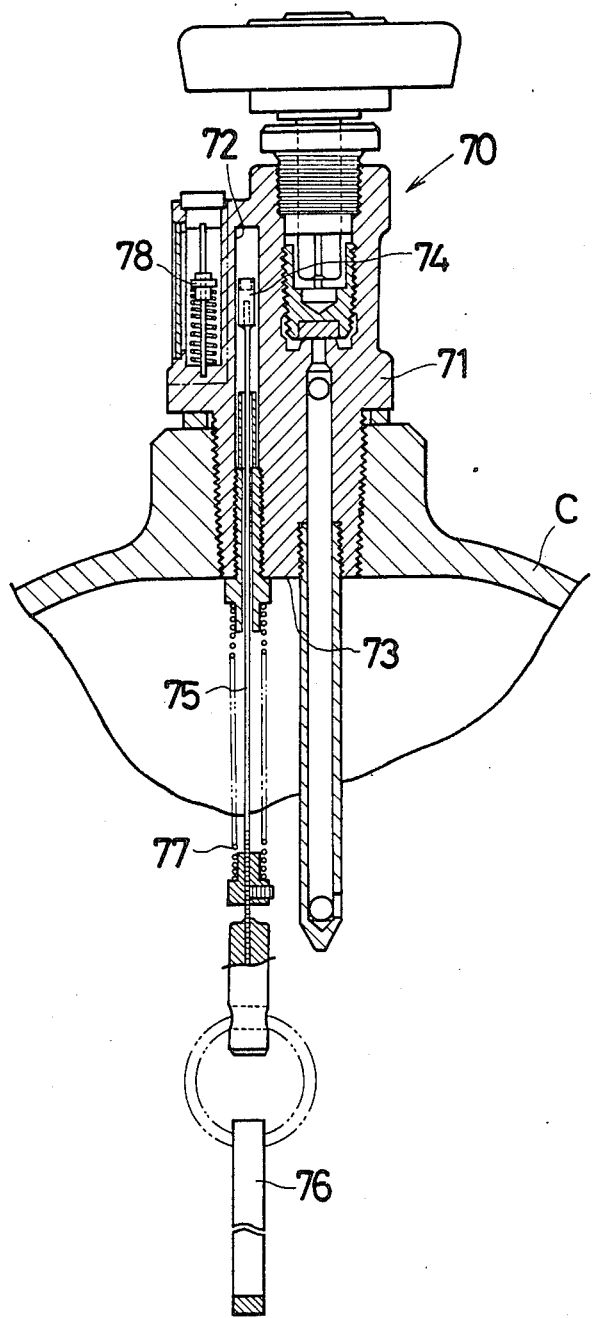

FIGS. 5 and 6 show the second embodiment. A structure different from that in the first embodiment will be explained hereinafter.

In this embodiment, instead of the above-mentioned peep window 22, a concavity 40 is formed at the peripheral wall 21 of the valve casing 6 so as to be arranged adjacent to the residual pressure measuring chamber 20, and a transparent tube 42 is disposed in the concavity 40 to provide a residual pressure indicating chamber 41 within the tube 42. The transparent tube 42 is provided with an upper end piece 43 and a lower end piece 43 respectively and secured to the concavity by a screw 44 through the end pieces 43, 43. And within the transparent tube 42 there is provided a cylindrical indicating piece 45 which is vertically movable by means of magnetic force.

On the other hand, a residual pressure indicating means 34 is provided on an upper portion 28c of a pressure actuator bar 28 and formed in a cylindrical configuration. One of or both of the residual pressure indicating means 34 and the residual pressure indicating piece 45 are composed of a magnet so that the piece 45 can be moved vertically within the transparent tube 42 following the vertical movement of the means 45.

Accordingly, since the present invention is constructed and functions as described above, the following advantages can be obtained.

(a) Since the pressure actuator bar which actuates the residual pressure indicating means is simply constructed so as to move vertically linearly slidably, the vibration-proof and the shock-proof thereof are greatly improved.

In a conventional Bourdon tube pressure gauge, a pointer happens to be locked by a damage of a pinion in a gear type magnifying mechanism when being shocked or vibrated. According to the present invention, such problems can be solved and always an residual pressure in the gas cylinder can be indicated accurately.

(b) Since the components such as the pressure actuator bar and the residual pressure indicating means etc are accommodated within the valve casing, they are protected thereby against collisions with other objects. Therefore, the indicator can be prevented from being broken or damaged by a falling down of the gas cylinder or a collision with other objects.

(c) Since the residual pressure within the gas cylinder is adapted to be indicated by the level of the residual pressure indicating means (or by the residual pressure indicating piece) and the level thereof is adapted to be observed readily from an outside of the valve casing, it can be confirmed over a wide range from a high pressure to a low pressure.

I claim:

1. A valve with a residual pressure indicator for a portable oxygen inhalant cylinder comprising: a valve chamber in a valve casing, an inlet port of the valve chamber opened at a bottom surface of the valve casing as well as an outlet port thereof opened at another surface thereof, a valve body in the valve chamber, a handle in the valve casing for opening and closing the valve body, and a residual pressure indicator for the cylinder in the valve casing, a residual pressure measuring chamber vertically located beside the inlet port in the valve casing, a through hole for a pressure actuator bar opening downwardly from a lower end portion of the residual pressure measuring chamber, a sealing means at the through hole so as to make contact with an intermediate portion of the pressure actuator bar and permitting vertical sliding movement thereof, a balancing spring connected to the lower portion of the pressure actuator bar so as to elastically force the bar downwardly, and a residual pressure indicating means on an upper portion of the pressure actuator bar so as to move vertically within the residual pressure measuring chamber.

2. A valve as recited in claim 1, wherein a peep window is provided on a peripheral wall of the residual pressure measuring chamber so that the residual pressure indicating means within the residual pressure measuring chamber can be observed through the peep window from outside of the valve casing.

3. A valve as recited in claim 1, wherein the residual pressure indicating means within the valve casing is provided at a portion adjacent to the residual pressure measuring chamber, a residual pressure indicating piece is vertically movably in the indicating chamber and being observed from outside thereof, and the indicating piece is adapted to be moved following the residual pressure indicating means by means of magnetic force.

4. A valve as recited in claim 1, wherein a spring support sleeve is connected to a foot portion of the valve casing downwardly, and the balancing spring is accommodated within the sleeve.

5. A valve as recited in claim 4, wherein the balancing spring comprises an extension spring, a lower end of the balancing spring is connected to the lower end of the spring support sleeve, and an upper end thereof is connected to the lower end portion of the pressure actuator bar.

6. A valve as recited in claim 4, wherein the balancing spring comprises a compression spring, the upper end of the balancing spring is supported by the foot portion of the valve casing, and the lower end thereof is connected to the lower portion of the pressure actuator bar so as to elastically force the bar downwardly.

7. A valve as recited in claim 1, wherein a transparent tube is fitted into the residual pressure measuring chamber from an under side thereof, a holder is secured airtightly to the lower portion of the measuring chamber so that the transparent tube is fixedly pushed to the upper wall of the measuring chamber by the upper end of the holder, the intermediate portion of the pressure actuator bar is passed through the hole of the holder vertically slidably air-tightly, the residual pressure indicating means in the interior of the transparent tube being movable vertically is adapted to be observed through the peep window from outside of the valve casing, and outside open air is communicated to the inner space within the transparent tube through a communicating passage such as a notch.

8. A valve as recited in claim 7, wherein there is provided a notch as the communicating passage on the upper end surface of the holder.

9. A valve as recited in claim 7, wherein the communication passage comprises at least ventilative one of an upper and a lower cushion members which are provided at opposed ends of the transparent tube respectively.

10. A valve as recited in claim 1, wherein at the periphery of the upper half of the valve casing, there is provided a gas outlet port, to which an inlet nozzle of an oxygen withdrawal means is connected air-tightly by a mounting frame fitted to the upper half of the valve casing.

11. A valve as recited in claim 1 or claim 9, wherein the upper half of the valve casing is formed in a rectangular configuration in a plan view and the inner periphery of the mount frame is formed in a rectangular configuration in a plan view.

12. A valve as recited in claim 9, wherein the inlet nozzle of the oxygen withdrawal means is connected to the outlet port provided at the upper half of the valve casing by threaded means.

* * * * *